Figure 1:
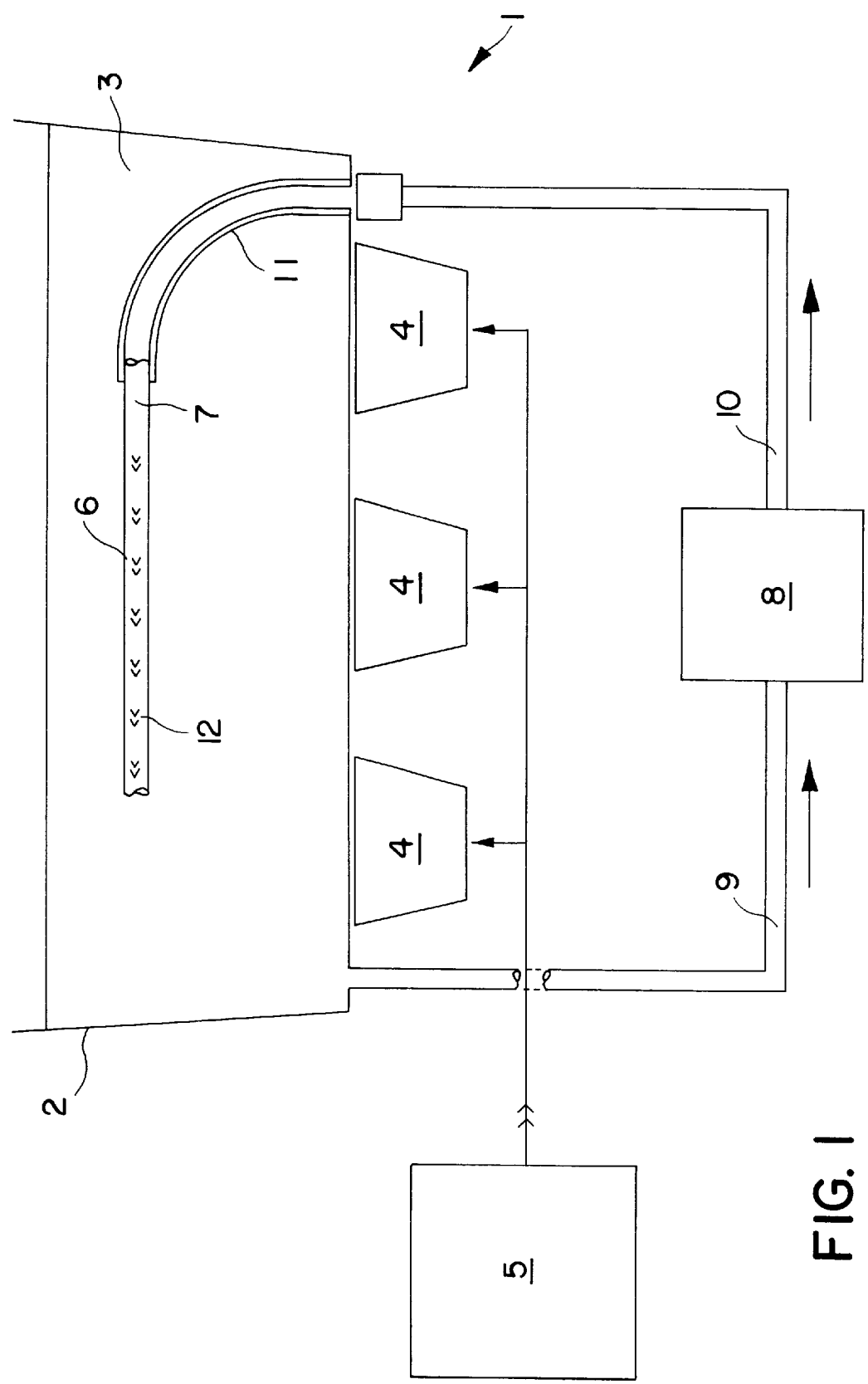

United States Patent
Dawson

[19]

[11] Patent Number: 5,985,038
[45] Date of Patent: *Nov. 16, 1999

[54] METHOD AND APPARATUS FOR CLEANING HOLLOW ELEMENTS

[76] Inventor: Lawrence Ralph Dawson, 17 Chelmsford House, Great Dunmow, Essex CM6 1EZ, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/945,445

[22] PCT Filed: Apr. 19, 1996

[86] PCT No.: PCT/GB96/00945

§ 371 Date: Dec. 29, 1997

§ 102(e) Date: Dec. 29, 1997

[87] PCT Pub. No.: WO96/33819

PCT Pub. Date: Oct. 31, 1996

[30] Foreign Application Priority Data

Apr. 24, 1995 [GB] United Kingdom ............... 9508279

[51] Int. Cl.[6] ............................................. B08B 3/12
[52] U.S. Cl. .................. 134/1; 134/22.18; 134/169 R; 134/170
[58] Field of Search ................. 134/1, 22.12, 22.18, 134/169 R, 169 A, 169 C, 170

[56] References Cited

U.S. PATENT DOCUMENTS 4,064,886 12/1977 Heckele .
5,147,464 9/1992 Skovron ........................................ 134/1
5,295,497 3/1994 Skovron ................................ 134/169 A

FOREIGN PATENT DOCUMENTS

| 5944202 | 4/1994 | European Pat. Off. . |
| 4140378 | 8/1993 | Germany . |
| 4432683 | 3/1996 | Germany . |
| 6-63012 | 3/1994 | Japan . |
| 6-343607 | 12/1994 | Japan . |
| 236579 A | 12/1994 | Taiwan . |
| 2289512 | 11/1995 | United Kingdom . |

OTHER PUBLICATIONS

Informal translation of the abstract and claims of foreign patent TW 236579 A.
Translation of Japanese Publication No. JP 6–63012.
Translation of Japanese Publication No. JP 6–343607.

*Primary Examiner*—Philip R. Coe
*Attorney, Agent, or Firm*—Alix Yale & Ristas, LLP

[57] ABSTRACT

A method and apparatus for cleaning hollow elements (6), such as medical instruments having cannulae, is disclosed in which a pulsed flow of cleaning fluid is passed through the element while ultrasonic waves are simultaneously applied to the fluid. The ultrasonic waves loosen any debris during the time when the fluid is substantially at rest, and the pulses of fluid then remove the debris. The apparatus can include a tank (2) containing cleaning fluid (3) into which the element is placed, the cleaning fluid being pumped from the tank into the hollow element. The frequency of the fluid pulses is preferably between zero and 300 Hz, and that of the ultrasonic waves is preferably greater than 15 kHz.

13 Claims, 1 Drawing Sheet

METHOD AND APPARATUS FOR CLEANING HOLLOW ELEMENTS

CROSS-REFERENCE TO RELATED APPLICATIONS

This is the national stage of International Application No. PCT/GB96/00945 filed Apr. 19, 1996.

This invention relates to a method and apparatus for cleaning hollow elements. In particular, the invention relates to the cleaning of medical and surgical instruments having hollow tubular elements which may be regular or irregular. However, the invention may also be used in the cleaning of other instruments or equipment having hollow or tubular bores or cavities. Examples are pipes, bores or valve blocks which are used to carry gas or fluid such as hydraulic fluid.

Many instruments used in the medical field, such as cannulae, comprise internal passageways through which, for example, surgical implements, fluids or catheters may be passed. An example of these are surgical instruments used to access internal parts of the body, such as laproscopic instruments, which may comprise a long tubular locating/gripping sleeve with a scissor-grip at one end which is connected inside the sleeve to a surgical tool, such as a cutter or grip, at the other end.

The cannulated instruments described above may either be constructed to be disposable or non-disposable, and the present invention is designed for cleaning either type. The non-disposable instruments, and in many cases even the disposable instruments, are often too expensive to be disposed of after only one use. Therefore, it is important that all internal and external surfaces of these instruments are thoroughly cleaned and disinfected in order to prevent the risk of passing on infection to other patients. Quite often, body fluid, tissue, or even pieces of bone can become lodged in the cannula of the instrument, which must be completely removed before the instrument is reused.

Traditionally, cannulae have been cleaned by hand by passing a brush along the passageway to dislodge any debris. Pressurised fluid is then passed through the cannula to wash out the loosened debris. Clearly, this is a time-consuming manual process, which requires the instrument to be dismantled, and it is quite possible that not all the debris will be removed, increasing the risk of cross-infection. Also, due to the construction of some instruments, it is not always possible to clean the cannulae by hand.

Another method of cleaning cannulated instruments is to use ultrasonic waves. The instruments are placed in a bath of cleaning fluid and the fluid is also pumped into the cannula. Ultrasonic transducers are then used to excite the fluid outside the instrument, and the excitation propagates through the instrument to the fluid in the cannula. The ultrasonic waves produce an effect in the fluid known as cavitation, in which tiny high pressure bubbles form and collapse at a high frequency. The effect of the expansion and collapse of these high pressure bubbles causes pressure waves which create a scrubbing action on the surfaces of the instrument, thereby dislodging any debris both inside and outside the instrument and cleaning all surfaces. The instrument is then removed from the cleaning fluid and is sterilised, which may be carried out by placing the instrument in an autoclave.

However, the application of ultrasonics to the cleaning fluid in the cavities does not provide a particularly efficient process because the debris remains inside the cannula once it has been dislodged by the cavitation. Debris or residue can then still be present in the cannula after the sterilisation stage. When an autoclave is used to sterilise the instrument, the debris or residue can even be "baked" back on to the surface of the instrument. This increases the risk of infection being passed to the next patient.

To overcome this problem, the applicants have developed a system in which the cleaning fluid is continuously pumped through the cannula of the instrument to be cleaned, while the ultrasonic waves are applied to the fluid. In this method, the instruments do not need to be dismantled as the fluid is pumped into the cannula through a specially provided opening. By providing a continuous moving stream of cleaning fluid, the debris removed by the ultrasonic excitation is flushed out in the cleaning fluid stream leaving the still unremoved debris exposed to the ultrasonically-excited fluid to be more easily removed. Therefore debris or residue is less likely to be present in the cannula after sterilisation.

However, because the cleaning fluid is continuously moving through the cannula, the effect of cavitation is reduced, firstly because the high pressure bubbles cannot form as easily in the moving stream and secondly because the transfer of ultrasonic power to the moving fluid in the cannula is not as efficient. Therefore, the speed with which the debris is removed from the surfaces of the instrument is increased when compared to the method employing still cleaning fluid in which the cavitation effect is greater.

The applicants have therefore identified a need for a system of cleaning the cannulae of, in particular but not exclusively, medical instruments which provides a more efficient cleaning effect.

Viewed from a first aspect, the invention provides a method of cleaning a hollow element by passing a pulsed flow of cleaning fluid through the element and simultaneously applying ultrasonic waves to the fluid.

Viewed from another aspect, the invention provides apparatus for cleaning a hollow element including means for providing a pulsed flow of cleaning fluid which is passed through the element and means for providing ultrasonic waves to the fluid.

By providing a pulsed flow of cleaning fluid inside the element, the fluid is substantially at rest for a time before it is moved on by the next pulse. During this rest time, the ultrasonic waves are able to more effectively penetrate the fluid, causing cavitation and an improved cleaning action. The fluid is then pushed along by the pulsing action, and this removes the debris which has been loosened by the ultrasonic waves while the fluid was substantially at rest. The applicants have found that stubborn debris and residues, and even small pieces of bone can be more efficiently removed by this process.

Preferably the fluid is pulsed by means of a linear or piston pump. This will then provide the necessary alternate still and moving pockets of fluid, as opposed to a constant pressure provided by some other types of pump. The fluid may be pulsed by other methods, such as the use of valves or the constriction of the supply.

The frequency of the pulses of fluid may vary depending on the particular application. However, in many applications it is envisaged that a frequency of between zero and 300 Hz provides a good cleaning effect.

The frequency of the ultrasonic waves is preferably greater than about 15 kHz. In preferred embodiments, the ultrasonic frequency is greater than about 30 kHz, and ideally between 30 and 36 kHz.

The cleaning fluid may simply be water, but preferably contains cleaning and/or disinfecting agents.

In preferred embodiments of the invention, the hollow element to be cleaned is placed in a tank of cleaning fluid, and the cleaning fluid is pulsed through the element. The ultrasonic waves are then preferably applied to the cleaning fluid in the tank, and the excitation propagates through the instrument to the fluid inside the element. The ultrasonic waves are preferably applied to the fluid by means of one or more transducers which may be located adjacent the edge of the tank, and which are preferably located on the outside of the tank. The transducers are preferably provided with an ultrasonic frequency signal from a frequency generator.

When a tank is employed, the cleaning fluid which is pulsed through the element is preferably the same as the fluid in the tank around the element. The fluid in the tank around the element is preferably supplied to the means for providing the pulsed flow, and in this way, the cleaning fluid is "cycled" from the tank to the means for providing the pulsed flow and through the element before returning to the tank. Preferably therefore, the apparatus further comprises a tank for containing the cleaning fluid, means for supplying the cleaning fluid in the tank to the means for providing a pulsed flow, and means for supplying the fluid from the means for providing a pulsed flow to the element. This latter means for supplying the fluid is preferably a flexible pipe.

An embodiment of the invention will now be described by way of example only and with reference to the accompanying FIG. 1 which shows a functional block diagram of cleaning apparatus employing the invention.

The cleaning apparatus shown generally as 1 comprises a tank 2 containing cleaning fluid 3. Ultrasonic transducers 4 are provided adjacent the tank 2 to supply the ultrasonic excitation to the fluid 3. The transducers 4 are provided with the ultrasonic frequency from a frequency generator 5.

A hollow element or cannula 6 which is to be cleaned is placed in the cleaning fluid 3. The element has a cavity 7. Optionally, a basket (not shown) may be provided in the tank 2 in which the elements to be cleaned are placed, so that the elements do not contact the bottom or sides of the tank and as much of the external surface of the elements as possible is exposed to the cleaning fluid.

In order to provide the pulsed flow of cleaning fluid to the cavity 7, a pump 8 is provided which is supplied with cleaning fluid from the tank through a pipe 9. The pump supplies pulsed cleaning fluid to the cavity 7 through a pipe 10 and a flexible tube 11, to which the element is connected.

To clean the element 6, the element is first placed in the empty tank 2 and connected to the pump 8 by flexible tube 11. The tank is then filled with cleaning fluid 3, and the pump is switched on to provide the pulsed fluid flow, shown by arrows 12, through the element at a predetermined frequency. Once the fluid flow is established, the ultrasonic frequency generator 5 is switched on and the ultrasound is supplied to the tank and fluid, thereby commencing the cleaning process. Once sufficient time has been allowed for the cleaning process to be completed, the tank can be drained and the elements removed and dried.

It is of course possible to clean more than one element at the same time, and in this case more than one flexible tube 11 may be provided which can be connected to each element and to the same pump or additional pumps as required.

I claim:

1. A method of cleaning a hollow medical instrument, comprising the steps of:
   providing a conduit attached to a pump means for providing a pulsed flow of cleaning fluid,
   providing a tank containing cleaning fluid,
   attaching the medical instrument to the conduit,
   immersing the medical instrument in the cleaning fluid in the tank,
   operating the pump means, thereby supplying the pulsed flow of cleaning fluid to the interior of the medical instrument,
   simultaneously with the supplying of the pulsed flow of cleaning fluid, applying ultrasonic waves to the fluid inside the medical instrument along the entire length of the instrument, the cleaning action being effected through the combined action of the pulsed flow of cleaning fluid and the ultrasonic waves, in which cavitation of the fluid inside the instrument is effective to loosen debris attached to the interior surface of the instrument, the debris being moved along the interior of the instrument by the pulses eventually to emerge from the instrument, and
   subsequently detaching the cleaned medical instrument from the conduit and removing it from the tank.

2. The method of claim 1 wherein the frequency of the pulses of fluid is between zero and 300 Hz.

3. The method of claim 1 wherein the frequency of the ultrasonic waves is greater than about 15 kHz.

4. The method of claim 1 wherein the frequency of the ultrasonic waves is greater than about 30 kHz.

5. The method of claim 1 wherein the frequency of the ultrasonic waves is between 30 and 36 kHz.

6. The method of claim 1 wherein the fluid is pulsed by means of a linear pump.

7. The method of claim 1 wherein the fluid is pulsed by means of a piston pump.

8. The method of claim 1 wherein the cleaning fluid contains cleaning agents.

9. The method of claim 1 wherein the cleaning fluid contains disinfecting agents.

10. The method of claim 1 wherein the medical instrument is a cannula.

11. The method of claim 1 wherein the medical instrument is immersed in the cleaning fluid after attachment to the conduit.

12. A method of cleaning a hollow medical instrument, comprising the steps of:
    providing a conduit attached to a pump means for providing a pulsed flow of cleaning fluid,
    providing a tank containing cleaning fluid,
    attaching the medical instrument to the conduit,
    immersing the medical instrument in the cleaning fluid in the tank,
    operating the pump means, thereby supplying the pulsed flow of cleaning fluid to the interior of the medical instrument,
    simultaneously with the supplying of the pulsed flow of cleaning fluid, applying ultrasonic waves to the fluid inside the medical instrument along the entire length of the instrument, the cleaning action being effected through the combined action of the pulsed flow of cleaning fluid and the ultrasonic waves, in which cavitation of the fluid inside the instrument between pulses is effective to loosen debris attached to the interior surface of the instrument, the debris being moved along the interior of the instrument by the pulses eventually to emerge from the instrument, and
    subsequently detaching the cleaned medical instrument from the conduit and removing it from the tank.

13. The method of claim 12 wherein the medical instrument is immersed in the cleaning fluid after attachment to the conduit.

* * * * *